United States Patent
Murugan et al.

(10) Patent No.: US 9,550,719 B2
(45) Date of Patent: Jan. 24, 2017

(54) PROCESS FOR THE PREPARATION OF 3-ARYL-2-HYDROXY PROPANOIC ACID COMPOUNDS

(71) Applicant: Council of Scientific and Industrial Research, New Delhi (IN)

(72) Inventors: Muthukrishnan Murugan, Pune (IN); Mujahid Mohammad, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 14/890,008

(22) PCT Filed: May 9, 2014

(86) PCT No.: PCT/IN2014/000322
§ 371 (c)(1),
(2) Date: Nov. 9, 2015

(87) PCT Pub. No.: WO2014/181362
PCT Pub. Date: Nov. 13, 2014

(65) Prior Publication Data
US 2016/0102042 A1    Apr. 14, 2016

(30) Foreign Application Priority Data

May 9, 2013 (IN) ............................ 1388/DEL/2013

(51) Int. Cl.
| | |
|---|---|
| *C07C 69/76* | (2006.01) |
| *C07C 67/08* | (2006.01) |
| *C07C 67/14* | (2006.01) |
| *C07C 41/16* | (2006.01) |
| *C07C 41/26* | (2006.01) |
| *C07C 41/30* | (2006.01) |
| *C07C 51/29* | (2006.01) |
| *C07C 51/367* | (2006.01) |
| *C07C 41/02* | (2006.01) |
| *C07C 41/09* | (2006.01) |

(52) U.S. Cl.
CPC ............... *C07C 67/08* (2013.01); *C07C 41/02* (2013.01); *C07C 41/09* (2013.01); *C07C 41/16* (2013.01); *C07C 41/26* (2013.01); *C07C 41/30* (2013.01); *C07C 51/29* (2013.01); *C07C 51/367* (2013.01); *C07C 67/14* (2013.01)

(58) Field of Classification Search
CPC .......... C07C 43/23; C07C 59/64; C07C 67/08; C07C 69/734; C07C 41/16; C07C 41/26; C07C 41/30; C07C 51/29; C07C 51/367; C07C 67/14; C07C 43/215; C07C 41/02; C07C 41/09
See application file for complete search history.

(56) References Cited

U.S. PATENT DOCUMENTS

| 6,559,335 B2 | 5/2003 | Kumar et al. |
|---|---|---|
| 2007/0149804 A1 | 6/2007 | Woltering et al. |
| 2015/0210632 A1* | 7/2015 | Zhu ........................ C07C 29/36 560/27 |

FOREIGN PATENT DOCUMENTS

| WO | WO-00/26200 A1 | 5/2000 |
|---|---|---|
| WO | WO-01/11073 A1 | 2/2001 |
| WO | WO-02/24625 A2 | 3/2002 |
| WO | WO-03/008362 A1 | 1/2003 |
| WO | WO-03/024915 A1 | 3/2003 |
| WO | WO-03/027084 A1 | 4/2003 |
| WO | WO-2005/019152 A2 | 3/2005 |
| WO | WO-2014/181362 | 11/2014 |

OTHER PUBLICATIONS

Kotsuki et al. (Ytterbium(III) Trifluoromethanesulfonate Catalyzed High Pressure Reaction of Epoxides with Indole. An Enantioselective Synthesis of (+)-Diolmycin A21, Tetrahedron Letters, vol. 37, No. 21. pp. 3727-3730, 1996).*

Boruwa et al. (Highly regioselective ring opening of epoxides using NaN3: a short and efficient synthesis of (−)-cytoxazone, Tetrahedron Letters 45 (2004) 7355-7358).*

"International Application No. PCT/IN2014/000322, International Search Report mailed Sep. 3, 2014", (Sep. 3, 2014), 3 pgs.

Brenna, Elisabetta, et al., "Enzyme-mediated synthesis of EEHP and EMHP, useful pharmaceutical intermediates of PPAR agonists", *Tetrahedron: Asymmetry*, 20(22), (2009), 2594-2599.

Brenna, Elisabetta, et al., "New stereospecific synthesis of Tesaglitazar and Navaglitazar precursors", *Tetrahedron: Asymmetry*, 20(23), (2009), 2694-2698.

Deussen, Heinz-Josef, et al., "Process Development on the Enantioselective Enzymatic Hydrolysis of S-Ethyl 2-Ethoxy-3-(4-hydroxyphenyl)propanoate", *Organic Process Research & Development*, 7(1), (2003), 82-88.

(Continued)

*Primary Examiner* — Yevegeny Valenrod
*Assistant Examiner* — Blaine G Doletski
(74) *Attorney, Agent, or Firm* — Schwegman Lundberg & Woessner, P.A.

(57) ABSTRACT

The present disclosure provides a process for synthesis of 3-aryl-2-hydroxy propanoic acid derivatives of formula (S)-1. wherein $R_1$ represents H or $(C_1-C_5)$ alkyl groups and $R_2$ represents $(C_1-C_5)$ alkyl groups.

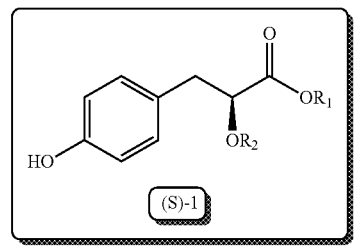

9 Claims, 1 Drawing Sheet

(56) References Cited

OTHER PUBLICATIONS

Harada, Hiroshi, et al., "Process Development of a Scaleable Route to (2R)-[3-(2-Aminopropyl)-1H-indol-7-yloxy]-N,N-diethylacetamide: A Key Intermediate for AJ-9677, a Potent and Selective Human and Rat $\beta_3$-Adrenergic Receptor Agonist", *Organic Process Research & Development*, 8(2), (2004), 238-245.

Houpis, Ioannis N., et al., "Synthesis of PPAR Agonist via Asymmetric Hydrogenation of a Cinnamic Acid Derivative and Stereospecific Displacement of (S)-2-Chloropropionic Acid", *Organic Letters*, 7(10), 2005, 1947-1950).

Mujahid, M., et al., "A new enantioselective synthesis of (S)-2-ethoxy-3-(4-hydroxyphenyl)propanoic acid esters (EEHP and IEHP), useful pharmaceutical intermediates of PPAR agonists", *Tetrahedron Letters*, 55(21), (2014), 3223-3226.

\* cited by examiner

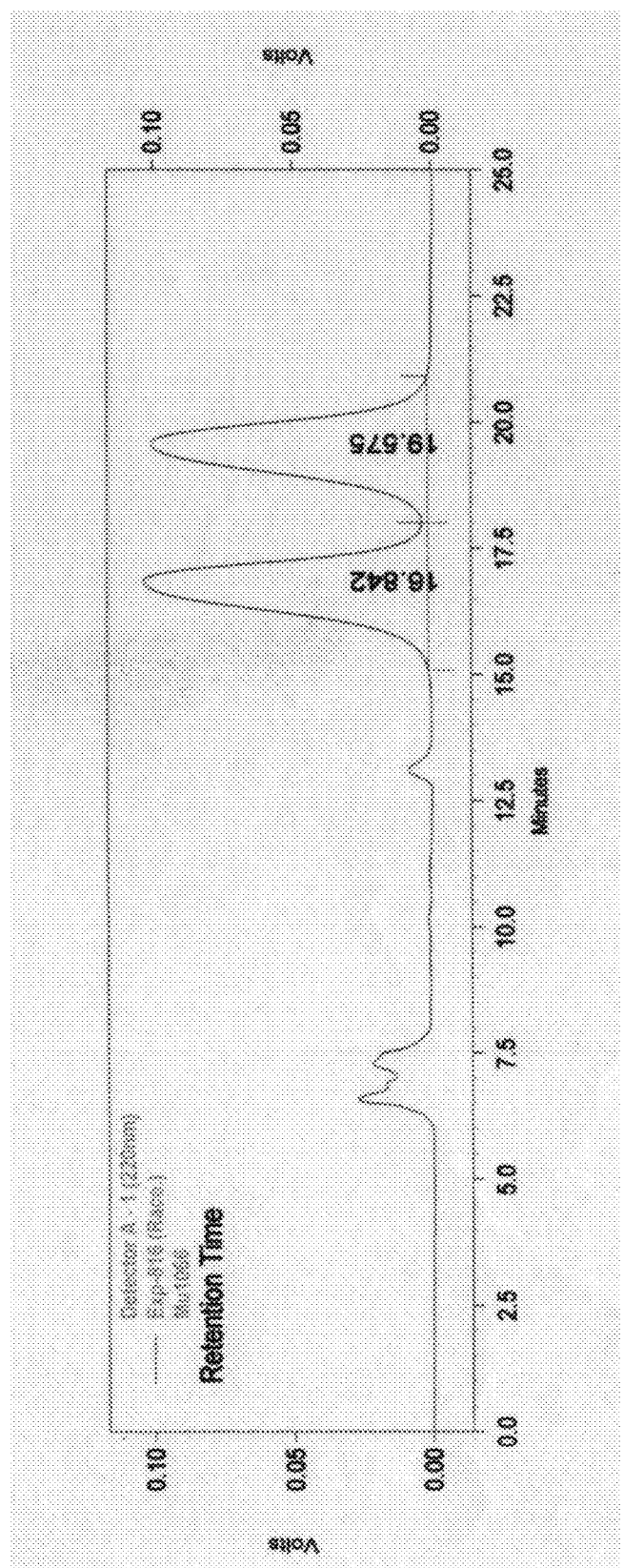

PROCESS FOR THE PREPARATION OF 3-ARYL-2-HYDROXY PROPANOIC ACID COMPOUNDS

PRIORITY CLAIM TO RELATED APPLICATIONS

This application is a U.S. national stage application filed under 35 U.S.C. §371 from International Application Serial No. PCT/IN2014/000322, which was filed 9 May 2014, and published as WO2014/181362 on 13 Nov. 2014, and which claims priority to India Application No. 1388/DEL/2013, filed 9 May 2013, which applications and publication are incorporated by reference as if reproduced herein and made a part hereof in their entirety, and the benefit of priority of each of which is claimed herein.

FIELD OF INVENTION

The present disclosure relates to a process for preparation of 3-aryl-2-hydroxy propanoic acid compounds of formula (S)-1.

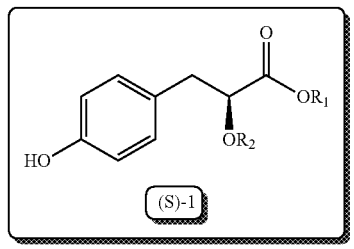

Wherein $R_1$ represents H or $(C_1-C_5)$ alkyl groups and $R_2$ represents $(C_1-C_5)$ alkyl groups.

BACKGROUND OF THE INVENTION

3-Aryl-2-hydroxy propanoic acid derivatives serve as a key intermediate for the synthesis of many pharmaceutically important compounds especially, peroxime proliferator activated receptor (PPAR) agonist. Optically active 3-aryl-2-alkoxy propanoic acid and its esters, particularly, ethyl (2S)-2-ethoxy-3-(4-hydroxyphenyl)propanoate (EEHP) and isopropyl (2S)-2-ethoxy-3-(4-hydroxyphenyl)propanoate (IEHP) are versatile chiral pharmacophores present in many pharmaceutically important compounds, especially in peroxisome proliferator activated receptor (PPAR) agonists that have beneficial effects in treating Type 2 diabetes. Several PPAR agonists, in particular PPAR α/γ dual agonists, commonly termed as glitazars (Ragaglitazar, Tesaglitazar, Navaglitazar etc.), as shown in the FIGURE below were developed by many pharmaceutical companies that have a potential application in the treatment of Type 2 diabetes and dyslipidemia. However, many of these drugs were discontinued due to their undesirable side effects, but some of them still have great potential [For example, Saraglitazar (Lipaglyn™) developed by Zydus Cadila got approval in India for the treatment of diabetic dyslipidemia or hypertriglyceridemia]. Several PPAR α/γ agonists possessing chiral (S)-1 moieties are shown below.

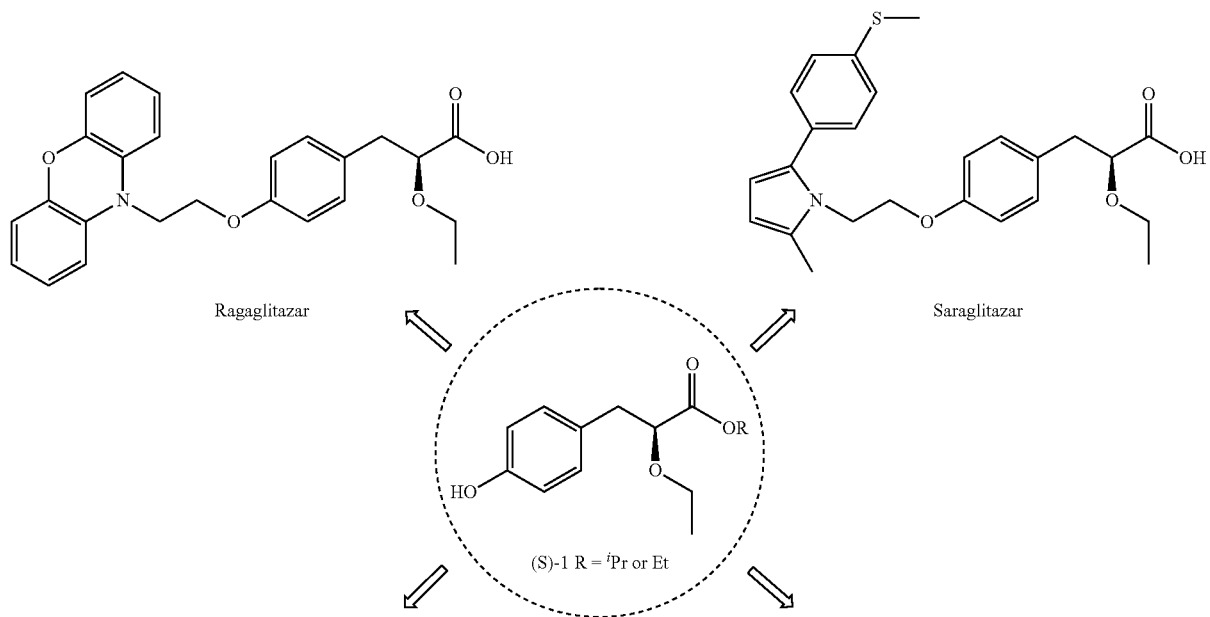

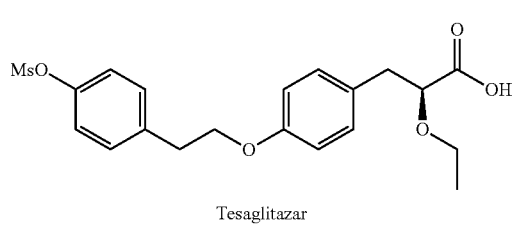

Tesaglitazar

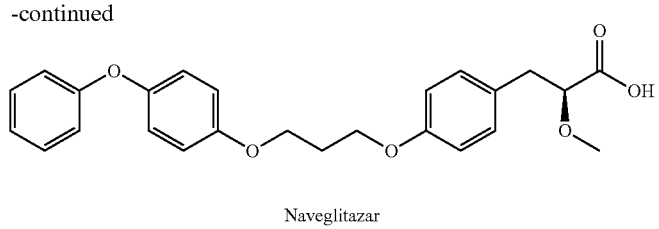

Naveglitazar

In addition, these derivatives find an application in photosensitive materials, sweetening agents, treatment of certain eating disorders etc. Therefore, these compounds have attracted a great deal of attention of synthetic chemists and different methods of preparation of the compound of formula (S)-1 have been extensively studied. Generally, the reported protocols for the synthesis involve chiral pool approaches starting from L-tyrosine and its derivatives (Refer WO 02/24625, U.S. Pat. No. 6,559,335B2, WO 2003/027084), asymmetric synthesis (*Org. Lett.* 2005, 7, 1947, US 2007/0149804) and resolution processes using chiral amines or enzymes (WO 2000/026200, WO 2001/11073, *Org. Process Res. Dev.* 2003, 7, 82, *Org. Process Res. Dev.* 2004, 8, 838, *Tetrahedron Asymmetry* 2009, 20, 2594). Some of these methods have disadvantages such as expensive chiral starting materials and catalysts, low enantioselectivity and overall yields, problems associated with the O-alkylation step which often leads to the loss of optical purity, and many others.

The processes described in WO20026200 (Rao et. al.) uses benzyl bromide for benzylation, which is highly lachrymatory. Again, in the processes described, the debenzylation of the final intermediate was done by using Pd/C under pressure, which escalates the process economics.

WO2003024915 describes a process for the preparation 3-aryl-2-hydroxy propanoic acid derivatives from 3-(4-hydroxyphenyl)-2-oxopropanoic acid.

WO 2003008362 describes 3-Aryl-2-hydroxy propanoic acid derivatives of formula I and the preparation thereof.

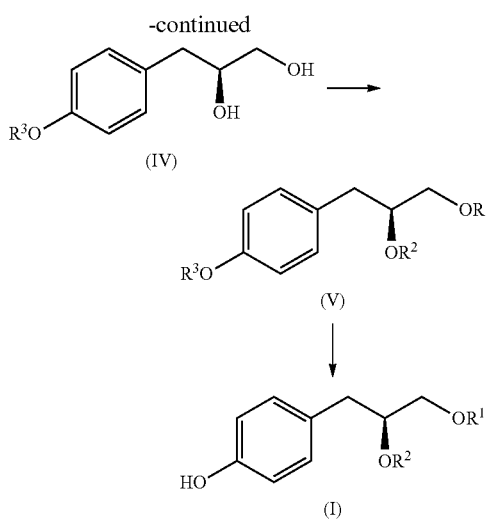

wherein R1 and R2 may be same or different and represent hydrogen or (C1-C6) alkyl.

The process includes i) reducing the compound of formula (III) where R represents hydrogen or alkyl group, R3 represents benzyl to a compound of formula (IV) where R3 represents benzyl, ii) etherifying the compound of formula (IV) using alkylating agent to a compound of formula (V) where R1, R2 and R3 are as defined above and iii) debenzylating the compound of formula (V) in the presence of metal catalysts to yield pure compound of formula (I).

The process is depicted in Scheme 1 below.

In another process variant as in Scheme 2, WO'362 discloses a process for the preparation of novel 3-aryl-2-hydroxy propanol and their derivatives of the formula (I)

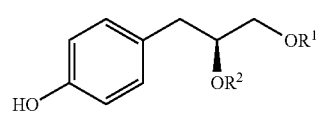

wherein OR and OR together form a substituted or unsubstituted 5 membered cyclic structure containing carbon and oxygen atoms, which comprises: i) reducing the compound of formula (III) where R represents hydrogen or alkyl group, R3 represents benzyl to a compound of formula (IV) where R3 represents benzyl, ii) cyclizing the compound of formula (IV) to a compound of formula (V) where OR1 and OR2 together form a substituted or unsubstituted 5 membered cyclic structure containing carbon and oxygen atoms and R3 represents benzyl and iii) debenzylating the compound of formula (V) in the presence of metal catalysts to yield pure compound of formula (I).

Scheme 1

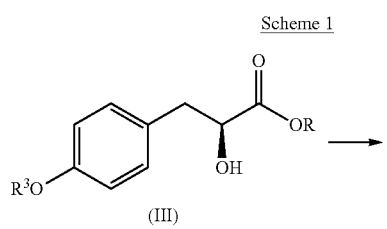

Scheme 2

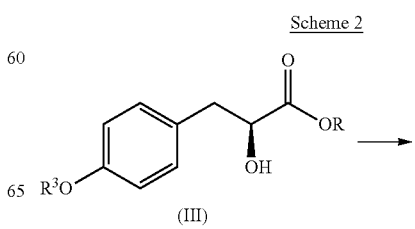

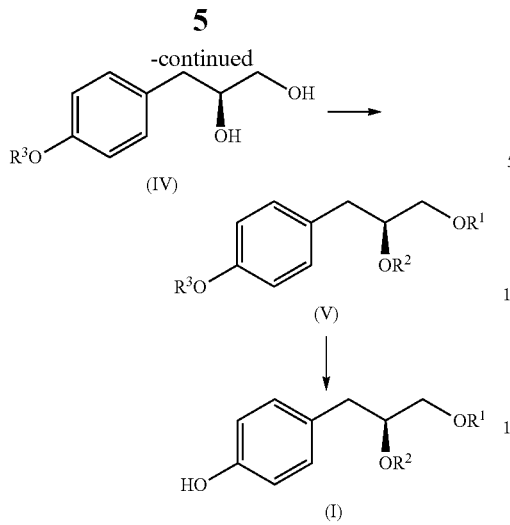

Both the processes described in WO'362 result in poor overall yield and further fail to describe the preparation of compound of formula V using different alkylating agents. This document exemplifies the compound of formula V with similar ether groups as it fails to teach selective alkylation of formula IV.

WO2005019152 discloses an improved process for the preparation of compound of the general formula (1a) and (1b).

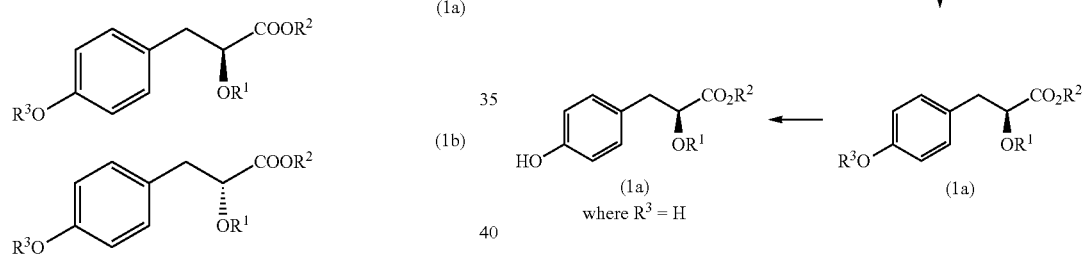

Wherein, R1 represent H or (C1-C6) alkyl group such as methyl, ethyl, propyl, isopropyl, butyl, isobutyl, t-butyl and the like. R2 represents (Ci-Ce) alkyl group such as methyl, ethyl, propyl, isopropyl, butyl, isobutyl, t-butyl and the like. R3 represents H, protecting groups such as benzyl, substituted benzyl, (C1-C3) alkyl and like.

The compound of general formula (1a) is prepared according to the following schemes 3 and 4.

Scheme 3

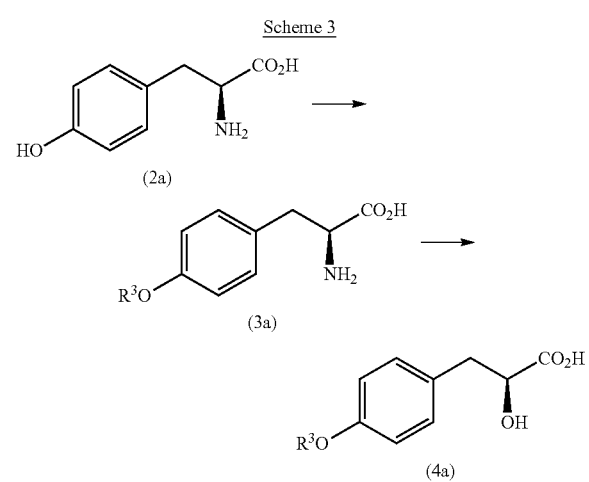

Scheme 4

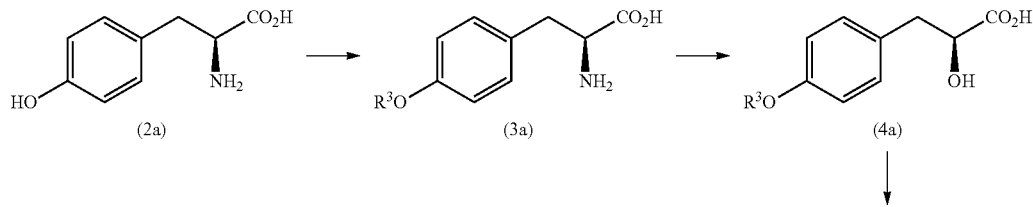

Both the processes start with selective O-alkylation or O-aralkylation of L-Tyrosine of formula (2a) using a base, a chelating agent, an alkyl or aralkyl halide in the presence of solvents to obtain the compound of formula (3a), which is diazotized to obtain formula (4a) which upon dialkylation using an excess of alkylating agent and excess base, in presence of suitable solvent to obtain optically pure compound of formula (1a). Alternatively, compound of formula (4a) may be selectively esterified to obtain compound of formula (5a), which is subsequently O-alkylated to obtain compound of formula (1a) (Scheme 2).

However, the above processes have many disadvantages such as multistep synthesis including protection & deprotection and low overall yield. Further, low temperature diazotization on industrial scale is not viable. Moreover, the starting material is very expensive and hence escalates the process.

In the light of the foregoing, development of a new, alternate enantio-selective synthetic route to these important chiral intermediates, which are simple and can preserve the optical purity at the C-2 carbon of 3-Aryl-2-hydroxy propanoic acid derivatives, is highly desirable. There is a need for an efficient process for synthesis of 3-Aryl-2-hydroxy propanoic acid derivatives of formula (S)-1 in high enantiopurity and good overall yield from commercially available starting material.

OBJECT OF INVENTION

The main object of the present disclosure is to provide a new and simple route for the preparation of the 3-aryl-2-hydroxy propanoic acid compounds of formula (S)-1 in high enantiopurity and good overall yield from commercially available starting material.

SUMMARY OF INVENTION

Accordingly, the present disclosure provides a process for the preparation of 3-aryl-2-hydroxy propanoic acid compounds of formula (S)-1, wherein $R_1$ represents H or $(C_1-C_5)$ alkyl groups and $R_2$ represents $(C_1-C_5)$ alkyl groups;

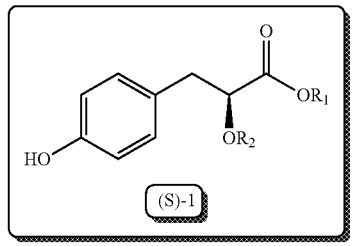

a) subjecting an epoxide (S)-2 to regioselective ring opening with 4-methoxyphenylmagnesium bromide in presence of (Copper iodide) CuI to obtain secondary alcohol (S)-3;

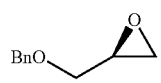

(S)-2

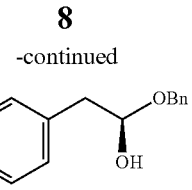

(S)-3 b) O-alkylating the secondary alcohol (S)-3 using ethyl iodide and a base in anhydrous DMF to give ethylated derivative (S)-4;

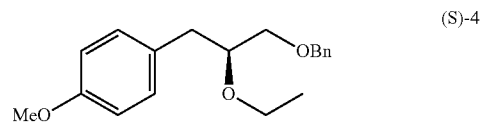 [SMILES: CCO[C@H](COCc1ccccc1)Cc1ccc(OC)cc1]

(S)-4 c) debenzylating (S)-4 in presence of a debenzylating agent to obtain primary hydroxy compound (S)-5;

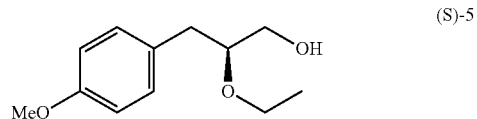

(S)-5 d. oxidizing the compound (S)-5 in presence of an oxidizing agent to obtain compound (S)-6; and

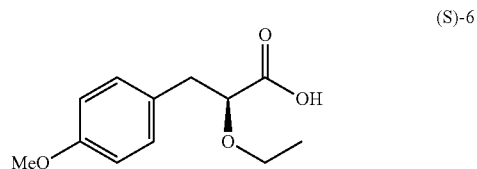 [SMILES: CCO[C@@H](Cc1ccc(OC)cc1)C(=O)O]

(S)-6 e. demethylating the compound (S)-6 using sodium ethanethiolate to obtain (S)-7 followed by esterification using EtOH and HCl to give (S)-1a;

f. optionally, esterificating of (S)-7 as obtained in step (e) using anhydrous 2-propanol and SOCl₂ to give (S)-1b.

In an embodiment of the present disclosure, the base used in step (b) is selected from NaOH, KOH, Na₂CO₃, or NaHCO₃.

In one embodiment of the present disclosure, the debenzylating agent used in step (c) is selected from Pd/C, Pd(OH)₂, Raney-Ni or TiCl₄ along with dichloromethane.

In an embodiment of the present disclosure, the oxidizing agent used in step (d) is selected from chromium trioxide along with H₂SO₄ or sodium chlorite/TEMPO/bleach conditions.

In another embodiment of the present disclosure, the compound of (S)-1a is

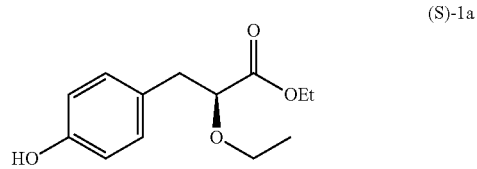 [SMILES: CCOC(=O)[C@H](Cc1ccc(O)cc1)OCC]

(S)-1a ethyl (2S)-2-ethoxy-3-(4-hydroxyphenyl)propanoate.

In an embodiment of the present disclosure, the compound of (S)-1b is isopropyl

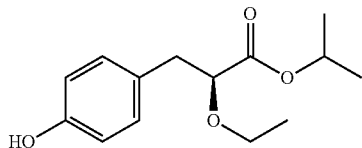

(S)-1b (2S)-2-ethoxy-3-(4-hydroxyphenyl)propanoate.

In an embodiment of the present disclosure, the overall yield of compound of (S)-1a is in the range of 40-45%.

In an embodiment of the present disclosure, the overall yield of compound of (S)-1b is in the range of 40-45%.

In an embodiment of the present disclosure, ee of 3-aryl-2-hydroxy propanoic acid compounds of formula (S)-1 is in the range of 97-99%.

BRIEF DESCRIPTION OF FIGURES

FIG. 1: Chiral HPLC chromatogram of (S)-1b.

DETAILED DESCRIPTION OF INVENTION

The present disclosure provides a process for the synthesis of the compound of formula (S)-1 starting from commercially available (S)-benzyl glycidyl ether in high enantiopurity of ee>99% and chemical yield of more than 43%.

Epoxides constitute one of the most widely used functional groups in organic transformations and serve as important building blocks in the industrial production of a wide variety of organic materials. As part of the study of the utility of epoxides on enantioselective transformations, the inventors of the present disclosure have put their interest in the application of epoxide to the synthesis of important chiral pharmaceuticals in the present disclosure for which protection is sought.

In view of the above, the present disclosure provides a process for the synthesis of the compound of formula (S)-1 starting from commercially available (S)-benzyl glycidyl ether in good overall yield and high enantiopurity of ee>99%.

The 3-aryl-2-hydroxy propanoic acid derivatives of (S)-1 according to the present disclosure encompasses ethyl (2S)-2-ethoxy-3-(4-hydroxyphenyl)propanoate (EEHP) (S)-1a and isopropyl (2S)-2-ethoxy-3-(4-hydroxyphenyl)propanoate (IEHP) (S)-1b.

The present disclosure provides a retrosynthetic analysis of compound of formula (S)-1 as shown in Scheme 5. The secondary alcohol (S)-3 can be visualized as a key intermediate for the synthesis which can be elaborated to primary hydroxy derivative (S)-5 using simple O-alkylation and debenzylation steps. Further, (S)-5 derivative can be transformed to the target molecule (S)-1 via oxidation followed by demethylation and esterification protocols. The key intermediate (S)-3 in turn can be obtained from commercially available (S)-benzyl glycidyl ether (S)-2.

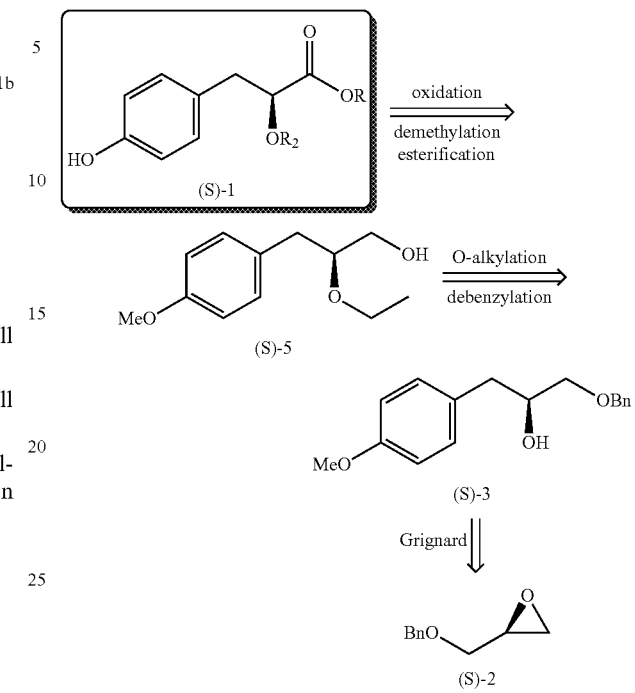

Scheme 5. Retrosynthetic analysis of (S)-1

The present disclosure commences with the commercially available, (S)-benzyl glycidylether (S)-2 which was subjected to regioselective ring opening with 4-methoxyphenylmagnesium bromide in the presence of catalytic amount of CuI in anhydrous THF at −20° C. to obtain the requisite key intermediate (S)-3 (Scheme 6). Further, O-ethylation on substrate (S)-3 was considered to be important, because of the fact that base mediated ethylation of α-hydroxy esters generally leads to epimerization at C-2 carbon. However, surprisingly, in the present case, the O-ethylation of protected secondary alcohol (S)-3 went smoothly with ethyliodide using sodium hydride as a base in DMF to produce O-ethylated derivative (S)-5 in 93% yield without any loss in optical purity. Therefore, it is important to consider that O-ethylation of protected hydroxyl derivative (S)-4 provides an attractive alternative to the alkylation of α-hydroxy ester derivatives to avoid the risk of epimerization at C-2 carbon. Further, compound (S)-4 was subjected to debenzylation followed by oxidation with sodium chlorite catalyzed by TEMPO and bleach in an acetonitrile-phosphate buffer (pH 6.8) afforded acid (S)-6 in 86% yield.

Finally, demethylation of compound (S)-6 was accomplished using NaH/EtSH in DMF at 130° C. to provide the acid (S)-7 in 86% yield. Other deprotection conditions such as BBr$_3$, HI etc were not favored as they are known to produce unwanted side products. Finally, the acid (S)-7 was esterified using ethanol under acidic condition to afford EEHP ((S)-1a) in 90% yield.

Similarly, IEHP ((S)-1b) was obtained by esterification of the acid (S)-7 with isopropanol (yield 85%; ee>99%). The structure of (S)-1a & (S)-1b was confirmed by its IR, 1H NMR, $^{13}$C NMR, and mass spectroscopic analysis. The enantiomeric excess of compounds (S)-1b and the intermediate (S)-3a was determined by chiral HPLC analysis.

Scheme 6 Synthesis of EEHP (S)-1a and IEHP (S)-1b

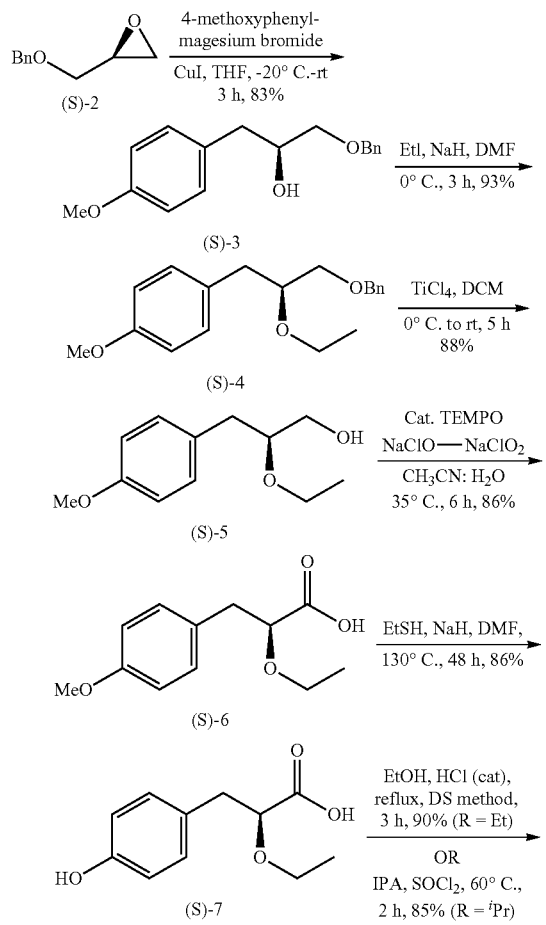

The process for the synthesis of 3-aryl-2-hydroxy propanoic acid derivatives comprises:
(a) regioselective ring opening of epoxide (S)-2 with 4-methoxyphenylmagnesium bromide to afford secondary alcohol of formula (S)-3;

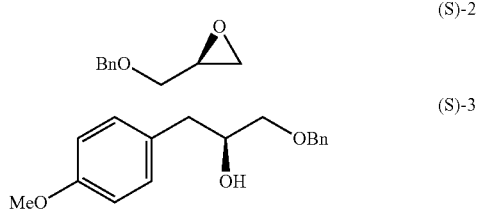

(b) O-alkylation of secondary alcohol (S)-3 of step (a) to give ethylated derivative (S)-4 without any loss in optical purity of final compound;

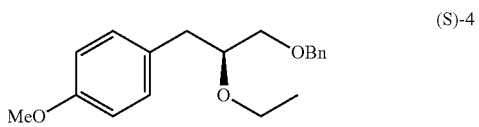 [SMILES: CCO[C@H](COCc1ccccc1)Cc1ccc(OC)cc1]

(c) debenzylation of compound (S)-4 of step (b) to furnish primary hydroxy compound (S)-5;

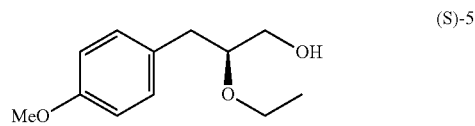

(d) oxidation of compound (S)-5 of step (c) to afford acid derivative (S)-6 and

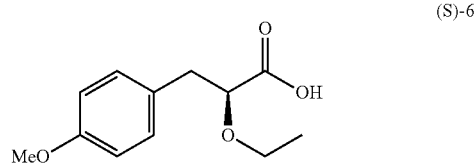 [SMILES: CCO[C@@H](Cc1ccc(OC)cc1)C(=O)O]

(e) demethylating of compound (S)-6 of step (d) followed by esterification to furnish the targeted compound of formula (S)-1.

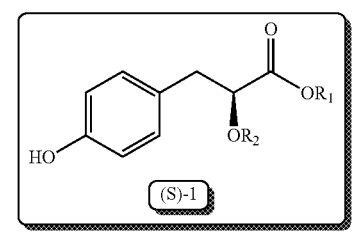

The present disclosure provides a process for the synthesis of the compound of formula (S)-1 depicted in Scheme 6 comprising the steps:
(a) subjecting the epoxide (S)-2 to the regioselective ring opening with 4-methoxyphenylmagnesium bromide in presence of CuI to afford secondary alcohol (S)-3 in 83% yield;
(b) O-alkylation of secondary alcohol (S)-3 using ethyl iodide and base in anhydrous DMF to give ethylated derivative (S)-4 in 93% yield without any loss in optical purity of final compound;
(c) debenzylation of compound (S)-4 to furnish primary hydroxy compound (S)-5 in 88% yield;
(d) oxidizing compound (S)-5 using TEMPO (2,2,6,6-tetramethyl-1-piperidinyloxyl) and bleach in acetonitrile-phosphate buffer (pH 6.8) condition to afford the corresponding acid (S)-6 in 86% yield; and
(e) demethylating of compound (S)-6 using sodium ethanethiolate followed by esterification using EtOH/HCl to give (S)-1a or IPA/SOCl$_2$ to give (S)-1b.

The base in step (b) is selected from NaOH, KOH, Na$_2$CO$_3$ and NaHCO$_3$. In a more preferred embodiment, the base is NaOH.

The agent for debenzylation is step (c) is selected from Pd/C, Pd(OH)$_2$, Raney-Ni and TiCl$_4$/dichloromethane, preferably TiCl$_4$/dichloromethane.

The oxidizing agent of step (d) is selected from chromium trioxide/H$_2$SO$_4$, (bis(acetoxy)iodo)benzene)/TEMPO and sodium chlorite, preferably sodium chlorite/2,2,6,6-tetramethyl-1-piperidinyl oxyl (TEMPO)/bleach conditions.

The structure of (S)-1a & (S)-1b was confirmed by its IR, $^1$H NMR, $^{13}$C NMR, and mass spectroscopic analysis. The enantiomeric purity was determined by chiral HPLC analysis as seen in FIG. 1.

EXAMPLES

The following examples are given by way of illustrations and therefore, should not be construed to limit the scope of the present investigation.

Solvents were purified and dried by standard procedures prior to use. IR spectra were obtained from Perking Elmer Spectrum one spectrophotometer. $^1$H NMR and $^{13}$C NMR spectra were recorded on a Bruker AC-200 NMR spectrometer. Spectra were obtained in CDCl$_3$. Monitoring of reactions was carried out using TLC plates Merck Silica Gel 60 F254 and visualization with UV light (254 and 365 nm), I$_2$ and anisaldehyde in ethanol as development reagents. Optical rotations were measured with a JASCO P 1020 digital polarimeter. Mass spectra were recorded at ionization energy 70 eV on API Q Star Pulsar spectrometer using electrospray ionization. Enantiomeric excess was determined by chiral HPLC.

Example 1

Preparation of (S)-1-(benzyloxy)-3-(4-methoxyphenyl) propan-2-ol referred as (S)-3

To a pre-cooled (−20° C.) solution of (S)-benzyl glycidyl ether (S)-2 (4.5 g, 27.4 mmol) and CuI (0.1 g) in dry THF (30 mL) was added 4-methoxyphenylmagnesium bromide (12 mL, 54.8 mmol) in THF (20 ml) drop-wise for about one hour. Subsequently, the reaction mixture was allowed to attain ambient temperature, usually 30° C. and continued the stirring for additional 4 h. After completion of the reaction (indicated by TLC), aqueous NH$_4$Cl 5 ml was added, after which the reaction mixture was filtered, and washed with ethyl acetate. The solvent was removed under reduced pressure and the crude product was subjected to column chromatography (silica gel, petroleum ether/acetone, 95:5) to yield (S)-3 as colorless oil. (6.1 g; 83%); $[\alpha]_D^{25}$=+11.3 (c 1.1, CHCl$_3$); IR (CHCl$_3$): 3387, 3019, 2977, 2933, 1612, 1496, 1454, 1370, 1296, 1216, 1104, 929, 757 cm$^{-1}$; $^1$H NMR (200 MHz, CDCl$_3$): $\delta_H$=2.76 (d, J=6.5 Hz, 2H), 3.43 (dd, J=9.5, 6.8 Hz, 1H), 3.54 (dd, J=9.5, 3.5 Hz, 1H), 3.79 (s, 3H), 3.95-4.07 (m, 1H), 4.54 (s, 2H), 6.86 (d, J=8.6 Hz, 2H), 7.10 (d, J=8.6 Hz, 2H), 7.31-7.37 (m, 5H); $^{13}$C NMR (50 MHz, CDCl$_3$): $\delta_C$=158.2 (C), 138.0 (C), 138.2 (CH, 2 carbons), 129.8 (C), 128.4 (CH, 2 carbons), 127.7 (CH, 3 carbons), 113.9 (CH, 2 carbons), 73.5 (CH$_2$), 73.3 (CH$_2$), 71.5 (CH), 55.3 (CH$_3$), 38.9 (CH$_2$); MS: m/z 295 [M+Na]$^+$.

Example 2

Preparation of (S)-1-(3-(benzyloxy)-2-ethoxypropyl)-4-methoxybenzene referred as (S)-4

In a 50 mL two-necked round bottomed flask sodium hydride (0.9 g, 36.5 mmol) was taken under N$_2$ atmosphere, and washed with pet ether followed by addition of dry DMF (15 mL). It was cooled to 0° C., then compound (S)-3 (4 g, 14.6 mmol) in dry DMF (3 mL) was added slowly. After stirring for 10 minutes, ethyl iodide (2.4 mL, 29.2 mmol) in 2 mL dry DMF was added slowly to the reaction mixture and again stirred at 0° C. for 1 h. After completion of the reaction (indicated by TLC), reaction was quenched with ice-cold water, extracted with ethyl acetate (3×15 mL). The combined organic layer was dried, concentrated under reduced pressure and purified using column chromatography (silica gel, petroleum ether/acetone, 97:3) to yield (S)-4 as colorless oil. (4.2 g; 93%); $[\alpha]_D^{25}$=−3.9 (c 1, CHCl$_3$); IR (CHCl$_3$): 3387, 3019, 2977, 2933, 1612, 1496, 1454, 1370, 1296, 1216, 1104, 929, 757 cm$^{-1}$; $^1$H NMR (200 MHz, CDCl$_3$): $\delta_H$=1.14 (t, J=6.7 Hz, 3H), 2.76-2.81 (m, 2H), 3.42-3.50 (m, 3H), 3.55-3.63 (m, 2H), 3.79 (s, 3H), 4.54 (s, 2H), 6.79 (d, J=8.6 Hz, 2H), 7.10 (d, J=8.6 Hz, 2H), 7.31-7.36 (m, 5H); $^{13}$C NMR (50 MHz, CDCl$_3$): $\delta_C$=157.3 (C), 137.7 (C), 130.1 (C), 129.7 (CH, 2 carbons), 127.6 (CH, 2 carbons), 127.0 (CH, 2 carbons), 126.8 (CH), 112.9 (CH, 2 carbons), 79.2 (CH), 72.6 (CH$_2$), 70.9 (CH$_2$), 64.8 (CH$_2$), 54.8 (CH$_3$), 36.6 (CH$_2$), 14.9 (CH$_3$); MS: m/z 323 [M+Na]+.

Example 3

Preparation of (S)-2-ethoxy-3-(4-methoxyphenyl) propan-1-ol referred to as (S)-5

To a solution of compound (S)-4 (4 g, 15.3 mmol) in dry DCM (10 mL) at 0° C. was added slowly TiCl$_4$ (2.5 mL, 23.0 mmol) under N$_2$ atmosphere. Subsequently, the reaction mixture was allowed to stir for 4 h at room temperature (30° C.). The reaction was quenched with saturated NH$_4$Cl solution and the mixture was allowed to stand for 1 h. The organic layer was separated and washed with 0.1 N HCl, saturated NaHCO$_3$ solution and brine. The organic layer was dried, concentrated under reduced pressure and purified using column chromatography (silica gel, petroleum ether/acetone, 80:20) to yield (S)-5 as colorless oil. (2.8 g; 88%); $[\alpha]_D^{25}$=+2.8 (c 1.8 CHCl$_3$); IR (CHCl$_3$): 3420, 3019, 1635, 1514, 1215, 1113, 928, 770, 669 cm$^{-1}$; $^1$H NMR (200 MHz, CDCl$_3$): $\delta_H$=1.23 (t, J=6.9 Hz, 3H), 2.64-2.82 (m, 2H), 3.47-3.61 (m, 5H), 3.80 (s, 3H), 3.91-3.95 (m, 1H), 6.86 (d, J=8.5 Hz, 2H), 7.15 (d, J=8.5 Hz, 2H); $^{13}$C NMR (50 MHz, CDCl3): $\delta_C$=157.0 (C), 130.3 (CH, 2 carbons), 130.3 (C), 113.8 (CH, 2 carbons), 81.1 (CH), 65.2 (CH$_2$), 63.2 (CH$_2$), 55.2 (CH$_3$), 36.4 (CH$_2$), 15.5 (CH$_3$); MS: m/z 211 [M+H]$^+$.

Example 4

Preparation of (S)-2-ethoxy-3-(4-methoxyphenyl) propanoic acid referred to as (S)-6

A mixture of (S)-5 (1 g, 4.4 mmol), TEMPO (2,2,6,6-Tetramethylpiperidine 1-oxyl) (0.034 g, 0.22 mmol), acetonitrile (20 mL), and sodium phosphate buffer (16 mL, 0.67 M, pH 6.7) was heated to 35° C. Then sodium chlorite (0.6 g dissolved in 2 mL water, 6.4 mmol) and dilute bleach (Sodium hypochlorite) (4-6%, 2 mL diluted in 4 mL water) were added simultaneously over 1 h. The reaction mixture was stirred at 35° C. until the reaction is complete (6 h, TLC), then cooled to room temperature. Water (20 mL) was added and the pH is adjusted to 8 with 2N NaOH. The reaction is quenched by pouring into ice cold Na$_2$SO$_3$ solution maintained at <20° C. After stirring for 30 min at room temperature, ethyl acetate (20 mL) was added and continued the stirring for additional 15 min. The organic layer was separated and discarded. More ethyl acetate (20 mL) was added, and the aqueous layer was acidified with 2N HCl to pH 3-4. The organic layer was separated, washed with water (2×15 mL), brine (20 mL) and concentrated under reduced pressure to afford the carboxylic acid (S)-6 (0.85 g, 86%); $[\alpha]_D^{25}=-15.3$ (c 2.7 CHCl$_3$); IR (CHCl$_3$): 3412, 3020, 1614, 1425, 1216, 1110, 1031, 928, 758 cm$^{-1}$; $^1$H NMR (200 MHz, CDCl$_3$): $\delta_H$=1.19 (t, J=7.0 Hz 3H), 2.90-3.15 (m, 2H), 3.39-3.65 (m, 2H), 3.80 (s, 3H), 4.03-4.16 (m, 1H), 6.87 (d, J=8.5 Hz 2H), 7.20 (d, J=8.5 Hz, 2H); $^{13}$C NMR (50 MHz, CDCl3): $\delta_C$=176.3 (CO), 158.5 (C), 130.4 (CH, 2 carbons), 128.6 (C), 113.7 (CH, 2 carbons), 79.7 (CH), 66.7 (CH$_2$), 55.1 (CH$_3$), 37.8 (CH$_2$), 14.9 (CH$_3$); MS: m/z 247 [M+Na]$^+$.

Example 5

Preparation of Ethyl (S)-2-ethoxy-3-(4-hydroxyphenyl)propanoate referred to as (S)-1a To a suspension of NaH (0.4 g, 60% disp. in min oil, 10 mmol) in DMF (5 mL) was added EtSH (Ethanethiol) (0.75 g, 12.0 mmol) under an N$_2$ atmosphere. After 30 min, a solution of acid (S)-6 (0.44 g, 2.0 mmol) in DMF (5 mL) was added. After 48 hrs at 130° C., the reaction mixture was quenched with a saturated solution of NaHCO$_3$ (40 mL) and washed with CH$_2$Cl$_2$ (3×20 mL). The aqueous phase was acidified with HCl (1 M) and extracted with EtOAc (3×20 mL). The combined organic phase was washed with brine (2×20 mL), dried over Na$_2$SO$_4$ and concentrated under reduced pressure to afford demethylated product (S)-7. To a stirred solution of (S)-7 (0.3 g) in EtOH (10 mL) was added conc. HCl (0.2 mL, 12 M) and the resulting mixture was heated to reflux at 80° C. for 3 h in a vessel well equipped with dean stark assembly for azeotropic removal of water formed in the reaction restoring the volume of ethanol. After completion of the reaction (Indicated by TLC), reaction mixture was concentrated under reduced pressure, diluted with ethyl acetate. The organic phase was washed with saturated NaHCO$_3$ solution and brine. The organic layer was dried, concentrated under reduced pressure and purified using column chromatography (silica gel, petroleum ether/ethyl acetate, 95:05) to afford (S)-1a 0.3 g, 90%) $[\alpha]_D^{25}=-26.9$ (c 0.4, CHCl$_3$), [lit. $[\alpha]_D^{25}=-21.3$ (c 1.45, CHCl$_3$) for 93% ee]; $^1$H NMR (200 MHz, CDCl$_3$): $\delta_H$=1.17 (t, J=6.9 Hz, 3H), 1.23 (t, J=6.9 Hz, 3H), 2.90 (d, J=7.0 Hz, 2H), 3.32-3.44 (m, 1H), 3.53-3.65 (m, 1H), 3.98 (t, J=6.6 Hz, 1H), 4.15 (dd, J=14.2, 7.0 Hz, 2H), 5.09 (bs, 1H), 6.77 (d, J=8.5 Hz, 2H), 7.13 (d, J=8.5 Hz, 2H); MS: m/z 239 [M+H]+261 [M+Na]+.

Example 7

Preparation of Isopropyl (S)-2-ethoxy-3-(4-hydroxyphenyl)propanoate referred to as (S)-1b To a stirred solution of (S)-7 (0.3 g, 1.4 mmol) in anhydrous 2-propanol (5 mL) was added thionyl chloride (0.2 mL, 2.6 mmol) slowly at room temperature (30° C.). The mixture was stirred for 2 h at 60° C. and solvent was removed under reduced pressure. Ethyl acetate was added and the organic layer was washed with 10% NaHCO$_3$ solution (2×15 mL), dried, concentrated under vacou and purified using column chromatography (silica gel, petroleum ether/ethyl acetate, 95:05). to furnish (S)-1b as oil (0.3 g; 85%); $[\alpha]_D^{25}=-19.4$ (c 1.02 CHCl$_3$) ee 99%; IR (CHCl$_3$): 3392, 3019, 2400, 1601, 1216, 1116, 928, 757 cm$^{-1}$; $^1$H NMR (200 MHz, CDCl$_3$): $\delta_H$=1.14-1.26 (m, 9H), 2.96 (d, J=6.6 Hz, 2H), 3.31-3.46 (m, 1H), 3.53-3.68 (m, 1H), 3.96 (t, J=6.6 Hz, 1H), 4.95-5.13 (m, 1H), 5.74 (bs, 1H), 6.75 (d, J=8.5 Hz, 2H), 7.11 (d, J=8.5 Hz, 2H); $^{13}$C NMR (50 MHz, CDCl3): $\delta_C$=172.3 (CO), 154.5 (C), 130.5 (CH, 2 carbons), 128.8 (C), 115.1 (CH, 2 carbons), 80.4 (CH), 68.5 (CH), 66.0 (CH$_2$), 38.3 (CH$_2$), 21.7 (CH$_3$), 21.6 (CH$_3$), 15.0 (CH$_3$); MS: m/z 275 [M+Na]$^+$. [The ee was determined by chiral HPLC analysis: Kromasil 5-Amycoat (250×4.6 mm) column; eluent: pet ether/ethanol=95/05; flow rate: 0.5 mL/min; detector 220 nm [(R) isomer $t_R$=16.53 min; (S) isomer $t_R$=19.01 min].

ADVANTAGES OF THE INVENTION

1. Commercially available starting material.
2. High enantiopurity (ee>99%) and good overall yield (>43%).

We claim:

1. A process for the preparation of 3-aryl-2-hydroxy propanoic acid compounds of formula (S)-1, wherein R$_1$ represents H or (C$_1$-C$_5$) alkyl groups and R$_2$ represents (C$_1$-C$_5$) alkyl groups, comprising the steps of;

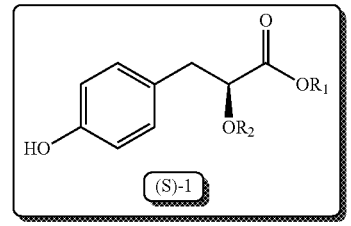

a) subjecting an epoxide (S)-2 to regioselective ring opening with 4-methoxyphenylmagnesium bromide in presence of copper iodide to obtain a secondary alcohol (S)-3;

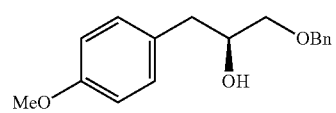

b) O-alkylating the secondary alcohol (S)-3 using ethyl iodide and a base in anhydrous DMF to give ethylated derivative (S)-4;

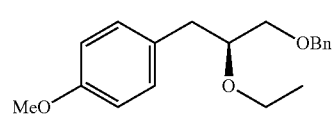

c) debenzylating (S)-4 in presence of a debenzylating agent to obtain primary hydroxy compound (S)-5;

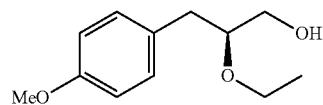
(S)-5 d. oxidizing the compound (S)-5 in presence of an oxidizing agent to obtain compound (S)-6; and

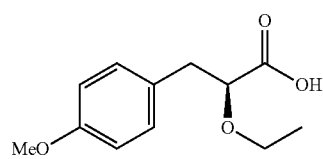
(S)-6 e. demethylating the compound (S)-6 using sodium ethanethiolate to obtain (S)-7 followed by esterification using EtOH and HCl to give (S)-1a;

f. optionally, esterificating of (S)-7 as obtained in step (e) using anhydrous 2-propanol and $SOCl_2$ to give (S)-1b.

2. The process according to claim 1, wherein the base used in step (b) is selected from NaOH, KOH, $Na_2CO_3$, or $NaHCO_3$.

3. The process according to claim 1, wherein the debenzylating agent used in step (c) is selected from Pd/C, $Pd(OH)_2$, Raney-Ni or $TiCl_4$ along with dichloromethane.

4. The process according to claim 1, wherein the oxidizing agent used in step (d) is selected from chromium trioxide along with $H_2SO_4$ or sodium chlorite along with TEMPO and sodium hypochlorite.

5. The process according to claim 1, wherein the compound of (S)-1a is ethyl (2S)-2-ethoxy-3-(4-hydroxyphenyl)propanoate,

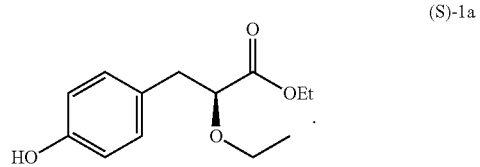 [SMILES: CCOC(=O)[C@H](Cc1ccc(O)cc1)OCC]
(S)-1a

6. The process according to claim 1, wherein the compound of (S)-1b is isopropyl (2S)-2-ethoxy-3-(4-hydroxyphenyl)propanoate,

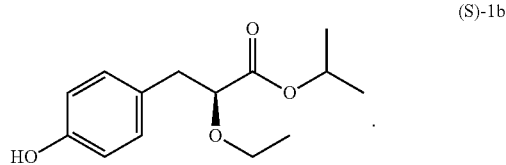 [SMILES: CCO[C@@H](Cc1ccc(O)cc1)C(=O)OC(C)C]
(S)-1b

7. The process according to claim 1, wherein overall yield of compound of (S)-1a is in the range of 40-45%.

8. The process according to claim 1, wherein overall yield of compound of (S)-1b is in the range of 40-45%.

9. The process according to claim 1, wherein enantiomeric excess (ee) of 3-aryl-2-hydroxy propanoic acid compounds of formula (S)-1 is in the range of 97-99%.

* * * * *